(12) United States Patent
Yanni et al.

(10) Patent No.: US 8,222,227 B2
(45) Date of Patent: Jul. 17, 2012

(54) RNAI-MEDIATED INHIBITION OF HISTAMINE RECEPTOR H1-RELATED CONDITIONS

(75) Inventors: John M. Yanni, Burleson, TX (US); Jon E. Chatterton, Fort Worth, TX (US); Daniel A. Gamache, Arlington, TX (US); Steven T. Miller, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/173,512

(22) Filed: Jun. 30, 2011

(65) Prior Publication Data
US 2011/0269822 A1 Nov. 3, 2011

Related U.S. Application Data

(62) Division of application No. 12/296,565, filed as application No. PCT/US2007/066287 on Apr. 10, 2007, now Pat. No. 8,017,592.

(60) Provisional application No. 60/791,623, filed on Apr. 13, 2006.

(51) Int. Cl.
*C12N 15/11* (2006.01)
(52) U.S. Cl. ........................................ 514/44 A
(58) Field of Classification Search .................. 514/44 A
See application file for complete search history.

(56) References Cited

U.S. PATENT DOCUMENTS

| | | | |
|---|---|---|---|
| 7,598,369 B2 | 10/2009 | Khvorova et al. | |
| 8,017,592 B2 * | 9/2011 | Yanni et al. | 514/44 R |
| 2005/0246794 A1 | 11/2005 | Khvorova et al. | |
| 2005/0255487 A1 * | 11/2005 | Khvorova et al. | 435/6 |
| 2008/0113351 A1 | 5/2008 | Naito et al. | |

FOREIGN PATENT DOCUMENTS
WO 2004094636 A1 11/2004

OTHER PUBLICATIONS

Altschul, et al.; Basic Local Alignment Search Tool; J. Mol. Biol. vol. 215; pp. 403-410; 1990.
Brummelkamp, et al.; "A system for stable expression of short interfering RNAs in mammalian cells"; vol. 296; pp. 550-553; Apr. 19, 2002.
Castanotto, et al; "Functional siRNA expression from transfected PCR products"; RNA; vol. 8; pp. 1454-1460; 2002.
Cook, et al.; "Isolation of human conjunctival mast cells and epithelial cells: tumor necrosis factor-alpha from mast cells affects intercellular adhesion molecule 1 expression on epithelial cells"; Investigative Ophthalmol Vis. Sci.; vol. 39; No. 2; pp: 336-343; Feb. 1998.
Iwata, et al.; "Biomodal regulation of the human H1 histamine receptor by G protein-coupled receptor kinase 2"; The Journal of Biological Chemistry; vol. 280; No. 3; pp: 2197-2204; Jan. 21, 2005.
Kawazoe, et al.; Chemical genetic identification of the histamine H1 receptor as a stimulator of insulin-induced adipogenesis; Chemistry & Biology; vol. 11; pp: 907-913; Jul. 2004.
Kim, et al.; "Synthetic dsRNA dicer substrates enhance RNAi potency and efficacy"; Nature Biotechnology; vol. 23; No. 2; pp. 222-226; Feb. 2005.
Offord, et al.; "Immortalized human corneal epithelial cells for ocular toxicity and inflammation studies"; Invest. Ophthalmol Vis. Science; vol. 40; pp. 1091-1101; 1999.
Sharif, et al.; Human corneal epithelial cell functional responses to inflammatory agents and their antagonists; Investigative Ophthalmology & Visual Science; vol. 39; No. 13; pp: 2562-2571; Dec. 1998.
Sharif, et al.; "Olopatadine (AL-4943A): ligand binding and functional studies on a novel, long acting H1-selective histamine antagonist and anti-allergic agent for use in allergic conjunctivitis"; Journal of Ocular Pharmacology and Therapeutics; vol. 12; No. 4; pp: 401-407; 1996.
Simmons; "Advances in H1-antihistamines"; The New England Journal of Medicine; vol. 35; pp: 2203-2217; Nov. 18, 2004.
Yanni, et al.; "Preclinical efficacy of Emedastine, a potent, selective histamine H1 antagonist for topical ocular use"; Journal of Ocular Pharmacology; vol. 10; No. 4; pp: 665-675 1994.
Dinh, et al.; "Transcriptional up-regulation of histamine receptor-1 in epithelial, mucus and inflammatory cells in perennial allergic rhinitis"; Clinical and Experimental Allergy; vol. 35, No. 11; pp. 1443-1448 (Nov. 2005).
Galeotti et al.; "Antihistamine antinociception is mediated by Gi-protein activation"; Neuroscience; vol. 109; No. 4; pp. 811-818 (Feb. 22, 2002).
Boese et al.; "Mechanistic insights aid computational short interfering RNA design"; Methods in Enzymology; vol. 392; [5] pp. 73-96; (2005).
Harborth et al.; "Identification of essential genes in cultured mammalian cells using small interfering RNAs"; Journal of Cell Science; vol. 114; pp. 4557-4565; (2001).
Holen et al.; "Positional effects of short interfering RNAs targeting the human coagulation trigger tissue factor"; Nucleic Acids Research; vol. 30; No. 8; pp. 1757-1766 (2002).
John et al.; Human MicroRNA Targets; PLOS Biology; www.plosbiology.org; vol. 2; Issue 11; pp. 1862-1879 (Nov. 2004).
Metzger et al.; Oligonucleotide Therapy of Allergic Asthma; J. Allergy Clin. Immunol.; vol. 102; pp. 260-266 (1999).
Moguilevsky et al; "Stable expression o Human H1-Histamine-Receptor cDNA in Chinese Hamster Ovary Cells"; Eur. J. Biochem.; vol. 224; pp. 489-495 (1994).
Reynolds et al.; "Rational siRNA design for RNA interference"; Nature Biotechnology; vol. 22; No. 3; pp. 326-330 (Mar. 2004).
International Search Report and European Search Report, dated Aug. 21, 2008 and Sep. 28, 2010, respectively.

* cited by examiner

*Primary Examiner* — Brian Whiteman
(74) *Attorney, Agent, or Firm* — Jason J. Derry

(57) ABSTRACT

RNA interference is provided for inhibition of histamine receptor H1 mRNA expression, in particular, for treating patients having an HRH1-related condition or at risk of developing an HRH1-related condition such as allergic conjunctivitis, ocular inflammation, dermatitis, rhinitis, asthma, or allergy.

13 Claims, No Drawings

SEQUENCE LISTING

```
<160> NUMBER OF SEQ ID NOS: 50

<210> SEQ ID NO 1
<211> LENGTH: 3870
<212> TYPE: DNA
<213> ORGANISM: Homo sapiens

<400> SEQUENCE: 1
cagggagaca tacaggattt aagaagccca tcatggagaa gaccttcaat tacagagata      60
aaaagttttt cttgtggaac aagttaacac tagatggcag ataacagact gaggagtgag     120
ctgcttctga ctcgattaaa aagggagtga gccataactg gcggctgctc tttcgccaat     180
gagcctcccc aattcctcct gcctcttaga agacaagatg tgtgagggca acaagaccac     240
tatggccagc ccccagctga tgccctggt ggtggtcctg agcactatct gcttggtcac      300
agtagggctc aacctgctgg tgctgtatgc cgtacggagt gagcggaagc tccacactgt     360
ggggaacctg tacatcgtca gcctctcggt ggcggacttg atcgtgggtg ccgtcgtcat     420
gcctatgaac atcctctacc tgctcatgtc caagtggtca ctgggccgtc ctctctgcct     480
cttttggctt tccatggact atgtgccag cacagcgtcc attttcagtg tcttcatcct      540
gtgcattgat cgctaccgct ctgtccagca gccctcagg taccttaagt atcgtaccaa       600
gacccgagcc tcggccacca ttctgggggc ctggtttctc tcttttctgt gggttattcc      660
cattctaggc tggaatcact tcatgcagca gacctcggtg cgccgagagg acaagtgtga     720
gacagacttc tatgatgtca cctggttcaa ggtcatgact gccatcatca acttctacct      780
gcccaccttg ctcatgctct ggttctatgc caagatctac aaggccgtac gacaacactg     840
ccagcaccgg gagctcatca ataggtccct cccttccttc tcagaaatta agctgaggcc     900
agagaacccc aaggggatg ccaagaaacc agggaaggag tctccctggg aggttctgaa      960
aaggaagcca aaagatgctg gtggtggatc tgtcttgaag tcaccatccc aaacccccaa    1020
ggagatgaaa tccccagttg tcttcagcca agaggatgat agagaagtag acaaactcta    1080
ctgctttcca cttgatattg tgcacatgca ggctgcggca gagggagta gcagggacta     1140 tgtagccgtc aaccggagcc atggccagct caagacagat gagcagggcc tgaacacaca    1200
tggggccagc gagatatcag aggatcagat gttaggtgat agccaatcct tctctcgaac    1260
```

```
ggactcagat accaccacag agacagcacc aggcaaaggc aaattgagga gtgggtctaa    1320
cacaggcctg gattacatca agtttacttg gaagaggctc cgctcgcatt caagacagta    1380
tgtatctggg ttgcacatga accgcgaaag gaaggccgcc aaacagttgg gttttatcat    1440
ggcagccttc atcctctgct ggatcccttta tttcatcttc ttcatggtca ttgccttctg    1500
caagaactgt tgcaatgaac atttgcacat gttcaccatc tggctgggct acatcaactc    1560
cacactgaac cccctcatct accccttgtg caatgagaac ttcaagaaga cattcaagag    1620
aattctgcat attcgctcct aagggaggct ctgaggggat gcaacaaaat gatccttatg    1680
atgtccaaca aggaaataga ggacgaaggc ctgtgtgttg ccaggcaggc acctgggctt    1740
tctggaatcc aaaccacagt cttagggggct tggtagtttg aaaagttctt aggcaccata    1800
gaagaacagc agatggcggt gatcagcaga gagattgaac tttgaggagg aagcagaatc    1860
tttgcaagaa agtcagacct gtttcttgta actgggttca aaaagaaaaa aataataaaa    1920
ataaaagaga gagagaatca gacctgggtg gaactctcct gctcctcagg aactatggga    1980
gcctcagact cattgtaatt caagcttttcc gagtcaagtg attgacaact gaagagacac    2040
gtggctaggg ttccactgga gaattgaaaa ggactcttga gccctcctgg aatggagctg    2100
tataactgtg cagagacttt atccatgcca atagttgctg tcccctccca ggggtcacct    2160
tgagaggcat gacagctgtt ccacaggggc tatcccttct cagaaaactt ctcttctgag    2220
cctctttaac agctttctcc agaaccagtg tctgaaccac cctggaaatt ctgccttatt    2280
atttcttact caaacatgtt tagagtggat agaaaattat gcagcttgca cacccatcat    2340 cttttaacccc aaatttcctt tggctattaa aaaagtggtg gcaaaaggca tcctcaaaag    2400
aaagagaaat gaaatatttt tgaatggttg cacgttaaaa attaaagaa ggaatggggg      2460 cagaatgcca tatttttgag ggctgtacta ggtttatctc atttaagccc cacaacaccc    2520
cacaggaggg taattttcta actctagttt gcagaggagc aaattgaggt tcagcaaggt    2580
gagagaggta cccaaggtca catagctagt tatgtgagaa agttagagta cagatcctct    2640 gggggtttcag cttattgtag catattttct ccgaaaggca aaaatgtgcc cttttggccg    2700
ggcatggtag ctcaagccta taatcccagc atgttgagag gctgaggtgg gcagatcatt    2760
tgaggccagg agttcaagac cagtctggcc aatatggaga aaccttgtct ctactaaaaa    2820
cacaaaaatt atctgggcat ggtggggcat gcctgtagtc ccacttactt gggaggccga    2880
ggcacgagaa tcgcttgaac ccgggaggtg gaggttgccg tgagccaaga tcacgccact    2940
gcactccagc ctgggcaaca gagcaagact ctgtctcaaa aaaaaaaata caatatttta    3000
acaatgtgcc ctcttaagtg tgcacagata cacatacacg gtattcccaa gagtggtggc    3060
agctcaaaat gatatgtttg agtagacgaa cagctgacat ggagttcccg tgcacctacg    3120
gaaggggacg ctttgaagga accaagtgca ttttatctg tgagttctgt tgtgtttgtc      3180
aaaaagtcat tgtaatcttt catagccata cctggtaagc aaaaactagt aaagacatag    3240
gaacatgtag ttttacttgg tgtttatgtt gcaatctggt tgtgatttat attttaaagc    3300
ttggtgctaa accacaatat gtatagcaca tggagtgcct gtacaagctg atgttttgta    3360
ttttgtgttc ctctttgcat gatctgtcaa agtgagatat ttttacctgc ctaaaatatg    3420
atgtttaaaa gcatactcta tgtgatttat ttatttctac cttctgagt ctcttggact      3480 aagaagatgt tttgaaatgt accatcaaat gttaacagag tttgatatgg gctttctctt    3540
tggtttctca tcacatttgt aaatgtcttt tcaaaaggat ttactttttg taaaagctt      3600 cattctcact ctgctttgca tccccccaaac ttcttgttca aaacgggggg agtttaggag    3660
```

```
actttaatcc cggtttcaga agctgcagct ggtctgtttc caggtcagaa accattgttc    3720
agaagacctc cctgtgagag agttgctcct cagggtccct caggaccaaa gaacactcga    3780
aaagagcact tcacacagac aagtggctaa gtgtccatta tttaccttga acaatcaagg    3840
caactagtgg agagaactga ttgtgagctc                                     3870

<210> SEQ ID NO 2
<211> LENGTH: 19
<212> TYPE: DNA
<213> ORGANISM: Artificial
<220> FEATURE:
<223> OTHER INFORMATION: Target Sequence

<400> SEQUENCE: 2
ctatctgctt ggtcacagt                                                 19

<210> SEQ ID NO 3
<211> LENGTH: 21
<212> TYPE: DNA
<213> ORGANISM: Artificial
<220> FEATURE:
<223> OTHER INFORMATION: Sense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: Misc_feature
<222> LOCATION: (20)..(21)
<223> OTHER INFORMATION: any, A, T/U, C. G

<400> SEQUENCE: 3
cuaucugcuu ggucacagun n                                              21

<210> SEQ ID NO 4
<211> LENGTH: 21
<212> TYPE: DNA
<213> ORGANISM: Artificial
<220> FEATURE:
<223> OTHER INFORMATION: Antisense strand with 3'NN
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: any, A, T/U, C. G

<400> SEQUENCE: 4
acugugacca agcagauagn n                                              21

<210> SEQ ID NO 5
<211> LENGTH: 21
<212> TYPE: RNA
<213> ORGANISM: Artificial
<220> FEATURE:
<223> OTHER INFORMATION: Sense Strand

<400> SEQUENCE: 5
cuaucugcuu ggucacaguu u                                              21

<210> SEQ ID NO 6
<211> LENGTH: 21
<212> TYPE: RNA
<213> ORGANISM: Artificial
<220> FEATURE:
<223> OTHER INFORMATION: Antisense Strand
```

```
<400> SEQUENCE: 6
acugugacca agcagauagu u                                              21

<210> SEQ ID NO 7
<211> LENGTH: 19
<212> TYPE: RNA
<213> ORGANISM: Artificial
<220> FEATURE:
<223> OTHER INFORMATION: Sense Strand

<400> SEQUENCE: 7
cuaucugcuu ggucacagu                                                 19

<210> SEQ ID NO 8
<211> LENGTH: 19
<212> TYPE: RNA
<213> ORGANISM: Artificial
<220> FEATURE:
<223> OTHER INFORMATION: Antisense Strand

<400> SEQUENCE: 8
acugugacca agcagauag                                                 19

<210> SEQ ID NO 9
<211> LENGTH: 48
<212> TYPE: DNA
<213> ORGANISM: Artificial
<220> FEATURE:
<223> OTHER INFORMATION: Hairpin duplex with loop
<220> FEATURE:
<221> NAME/KEY: misc_RNA
<222> LOCATION: (1)..(19)
<223> OTHER INFORMATION: ribonucleotides
<220> FEATURE:
<221> NAME/KEY: misc_feature
<222> LOCATION: (20)..(27)
<223> OTHER INFORMATION: any, A, T/U, C, G
<220> FEATURE:
<221> NAME/KEY: misc_feature
<222> LOCATION: (28)..(48)
<223> OTHER INFORMATION: ribonucleotides

<400> SEQUENCE: 9
cuaucugcuu ggucacagun nnnnnnnacu gugaccaagc agauaguu                 48

<210> SEQ ID NO 10
<211> LENGTH: 25
<212> TYPE: DNA
<213> ORGANISM: Artificial
<220> FEATURE:
<223> OTHER INFORMATION: Sense Strand

<400> SEQUENCE: 10
ctatctgctt ggtcacagta gggct                                          25

<210> SEQ ID NO 11
<211> LENGTH: 25
<212> TYPE: RNA
<213> ORGANISM: Artificial
<220> FEATURE:
<223> OTHER INFORMATION: Sense Strand

<400> SEQUENCE: 11
cuaucugcuu ggucacagua gggcu                                          25

<210> SEQ ID NO 12
<211> LENGTH: 27
```

```
<212> TYPE: RNA
<213> ORGANISM: Artificial
<220> FEATURE:
<223> OTHER INFORMATION: Antisense Strand

<400> SEQUENCE: 12
agcccuacug ugaccaagca gauaguu                                            27

<210> SEQ ID NO 13
<211> LENGTH: 19
<212> TYPE: DNA
<213> ORGANISM: Artificial
<220> FEATURE:
<223> OTHER INFORMATION: Target Sequence

<400> SEQUENCE: 13
tgtatgccgt acggagtga                                                     19

<210> SEQ ID NO 14
<211> LENGTH: 19
<212> TYPE: DNA
<213> ORGANISM: Artificial
<220> FEATURE:
<223> OTHER INFORMATION: Target Sequence

<400> SEQUENCE: 14
gccgtcgtca tgcctatga                                                     19

<210> SEQ ID NO 15
<211> LENGTH: 19
<212> TYPE: DNA
<213> ORGANISM: Artificial
<220> FEATURE:
<223> OTHER INFORMATION: Target Sequence

<400> SEQUENCE: 15
taccttaagt atcgtacca                                                     19

<210> SEQ ID NO 16
<211> LENGTH: 19
<212> TYPE: DNA
<213> ORGANISM: Artificial
<220> FEATURE:
<223> OTHER INFORMATION: Target Sequence

<400> SEQUENCE: 16
cttaagtatc gtaccaaga                                                     19

<210> SEQ ID NO 17
<211> LENGTH: 19
<212> TYPE: DNA
<213> ORGANISM: Artificial
<220> FEATURE:
<223> OTHER INFORMATION: Target Sequence

<400> SEQUENCE: 17
ccattctagg ctggaatca                                                     19

<210> SEQ ID NO 18
<211> LENGTH: 19
<212> TYPE: DNA
<213> ORGANISM: Artificial
<220> FEATURE:
<223> OTHER INFORMATION: Target Sequence

<400> SEQUENCE: 18
ggaatcactt catgcagca                                                     19
```

```
<210> SEQ ID NO 19
<211> LENGTH: 19
<212> TYPE: DNA
<213> ORGANISM: Artificial
<220> FEATURE:
<223> OTHER INFORMATION: Target Sequence

<400> SEQUENCE: 19
ggttctatgc caagatcta                                                  19

<210> SEQ ID NO 20
<211> LENGTH: 19
<212> TYPE: DNA
<213> ORGANISM: Artificial
<220> FEATURE:
<223> OTHER INFORMATION: Target Sequence

<400> SEQUENCE: 20
ctacaaggcc gtacgacaa                                                  19

<210> SEQ ID NO 21
<211> LENGTH: 19
<212> TYPE: DNA
<213> ORGANISM: Artificial
<220> FEATURE:
<223> OTHER INFORMATION: Target Sequence

<400> SEQUENCE: 21
cagccaagag gatgataga                                                  19

<210> SEQ ID NO 22
<211> LENGTH: 19
<212> TYPE: DNA
<213> ORGANISM: Artificial
<220> FEATURE:
<223> OTHER INFORMATION: Target Sequence

<400> SEQUENCE: 22
atagagaagt agacaaact                                                  19

<210> SEQ ID NO 23
<211> LENGTH: 19
<212> TYPE: DNA
<213> ORGANISM: Artificial
<220> FEATURE:
<223> OTHER INFORMATION: Target Sequence

<400> SEQUENCE: 23
cacttgatat tgtgcacat                                                  19

<210> SEQ ID NO 24
<211> LENGTH: 19
<212> TYPE: DNA
<213> ORGANISM: Artificial
<220> FEATURE:
<223> OTHER INFORMATION: Target Sequence

<400> SEQUENCE: 24
agccatggcc agctcaaga                                                  19

<210> SEQ ID NO 25
<211> LENGTH: 19
<212> TYPE: DNA
<213> ORGANISM: Artificial
<220> FEATURE:
<223> OTHER INFORMATION: Target Sequence
```

```
<400> SEQUENCE: 25
gcgagatatc agaggatca                                              19

<210> SEQ ID NO 26
<211> LENGTH: 19
<212> TYPE: DNA
<213> ORGANISM: Artificial
<220> FEATURE:
<223> OTHER INFORMATION: Target Sequence

<400> SEQUENCE: 26
gatcagatgt taggtgata                                              19

<210> SEQ ID NO 27
<211> LENGTH: 19
<212> TYPE: DNA
<213> ORGANISM: Artificial
<220> FEATURE:
<223> OTHER INFORMATION: Target Sequence

<400> SEQUENCE: 27
agccaatcct tctctcgaa                                              19

<210> SEQ ID NO 28
<211> LENGTH: 19
<212> TYPE: DNA
<213> ORGANISM: Artificial
<220> FEATURE:
<223> OTHER INFORMATION: Target Sequence

<400> SEQUENCE: 28
tctcgaacgg actcagata                                              19

<210> SEQ ID NO 29
<211> LENGTH: 19
<212> TYPE: DNA
<213> ORGANISM: Artificial
<220> FEATURE:
<223> OTHER INFORMATION: Target Sequence

<400> SEQUENCE: 29
tcagatacca ccacagaga                                              19

<210> SEQ ID NO 30
<211> LENGTH: 19
<212> TYPE: DNA
<213> ORGANISM: Artificial
<220> FEATURE:
<223> OTHER INFORMATION: Target Sequence

<400> SEQUENCE: 30
ctcgcattca agacagtat                                              19

<210> SEQ ID NO 31
<211> LENGTH: 19
<212> TYPE: DNA
<213> ORGANISM: Artificial
<220> FEATURE:
<223> OTHER INFORMATION: Target Sequence

<400> SEQUENCE: 31
ttgcacatga accgcgaaa                                              19

<210> SEQ ID NO 32
<211> LENGTH: 19
```

```
<212> TYPE: DNA
<213> ORGANISM: Artificial
<220> FEATURE:
<223> OTHER INFORMATION: Target Sequence

<400> SEQUENCE: 32
tcattgcctt ctgcaagaa                                                    19

<210> SEQ ID NO 33
<211> LENGTH: 19
<212> TYPE: DNA
<213> ORGANISM: Artificial
<220> FEATURE:
<223> OTHER INFORMATION: Target Sequence

<400> SEQUENCE: 33
atttgcacat gttcaccat                                                    19

<210> SEQ ID NO 34
<211> LENGTH: 19
<212> TYPE: DNA
<213> ORGANISM: Artificial
<220> FEATURE:
<223> OTHER INFORMATION: Target Sequence

<400> SEQUENCE: 34
tctgcatatt cgctcctaa                                                    19

<210> SEQ ID NO 35
<211> LENGTH: 19
<212> TYPE: DNA
<213> ORGANISM: Artificial
<220> FEATURE:
<223> OTHER INFORMATION: Target Sequence

<400> SEQUENCE: 35
tgatccttat gatgtccaa                                                    19

<210> SEQ ID NO 36
<211> LENGTH: 19
<212> TYPE: DNA
<213> ORGANISM: Artificial
<220> FEATURE:
<223> OTHER INFORMATION: Target Sequence

<400> SEQUENCE: 36
tccttatgat gtccaacaa                                                    19

<210> SEQ ID NO 37
<211> LENGTH: 19
<212> TYPE: DNA
<213> ORGANISM: Artificial
<220> FEATURE:
<223> OTHER INFORMATION: Target Sequence

<400> SEQUENCE: 37
agttcttagg caccataga                                                    19

<210> SEQ ID NO 38
<211> LENGTH: 19
<212> TYPE: DNA
<213> ORGANISM: Artificial
<220> FEATURE:
<223> OTHER INFORMATION: Target Sequence

<400> SEQUENCE: 38
tcagacctgt ttcttgtaa                                                    19
```

```
<210> SEQ ID NO 39
<211> LENGTH: 19
<212> TYPE: DNA
<213> ORGANISM: Artificial
<220> FEATURE:
<223> OTHER INFORMATION: Target Sequence

<400> SEQUENCE: 39
agacctgttt cttgtaact                                                  19

<210> SEQ ID NO 40
<211> LENGTH: 19
<212> TYPE: DNA
<213> ORGANISM: Artificial
<220> FEATURE:
<223> OTHER INFORMATION: Target Sequence

<400> SEQUENCE: 40
cagactcatt gtaattcaa                                                  19

<210> SEQ ID NO 41
<211> LENGTH: 19
<212> TYPE: DNA
<213> ORGANISM: Artificial
<220> FEATURE:
<223> OTHER INFORMATION: Target Sequence

<400> SEQUENCE: 41
cctggaatgg agctgtata                                                  19

<210> SEQ ID NO 42
<211> LENGTH: 19
<212> TYPE: DNA
<213> ORGANISM: Artificial
<220> FEATURE:
<223> OTHER INFORMATION: Target Sequence

<400> SEQUENCE: 42
ctggaatgga gctgtataa                                                  19

<210> SEQ ID NO 43
<211> LENGTH: 19
<212> TYPE: DNA
<213> ORGANISM: Artificial
<220> FEATURE:
<223> OTHER INFORMATION: Target Sequence

<400> SEQUENCE: 43
ttaacagctt tctccagaa                                                  19

<210> SEQ ID NO 44
<211> LENGTH: 19
<212> TYPE: DNA
<213> ORGANISM: Artificial
<220> FEATURE:
<223> OTHER INFORMATION: Target Sequence

<400> SEQUENCE: 44
tgtttagagt ggatagaaa                                                  19

<210> SEQ ID NO 45
<211> LENGTH: 19
<212> TYPE: DNA
<213> ORGANISM: Artificial
<220> FEATURE:
<223> OTHER INFORMATION: Target Sequence
```

```
<400> SEQUENCE: 45
ttgaatggtt gcacgttaa                                                19

<210> SEQ ID NO 46
<211> LENGTH: 19
<212> TYPE: DNA
<213> ORGANISM: Artificial
<220> FEATURE:
<223> OTHER INFORMATION: Target Sequence

<400> SEQUENCE: 46
tgaatggttg cacgttaaa                                                19

<210> SEQ ID NO 47
<211> LENGTH: 19
<212> TYPE: DNA
<213> ORGANISM: Artificial
<220> FEATURE:
<223> OTHER INFORMATION: Target Sequence

<400> SEQUENCE: 47
gtactaggtt tatctcatt                                                19

<210> SEQ ID NO 48
<211> LENGTH: 19
<212> TYPE: DNA
<213> ORGANISM: Artificial
<220> FEATURE:
<223> OTHER INFORMATION: Target Sequence

<400> SEQUENCE: 48
tagctagtta tgtgagaaa                                                19

<210> SEQ ID NO 49
<211> LENGTH: 19
<212> TYPE: DNA
<213> ORGANISM: Artificial
<220> FEATURE:
<223> OTHER INFORMATION: Target Sequence

<400> SEQUENCE: 49
tcagcttatt gtagcatat                                                19

<210> SEQ ID NO 50
<211> LENGTH: 19
<212> TYPE: DNA
<213> ORGANISM: Artificial
<220> FEATURE:
<223> OTHER INFORMATION: Target Sequence

<400> SEQUENCE: 50
gcatactcta tgtgattta                                                19
```

US 8,222,227 B2

RNAI-MEDIATED INHIBITION OF HISTAMINE RECEPTOR H1-RELATED CONDITIONS

The present application is a divisional of U.S. application Ser. No. 12/296,565 filed Oct. 9, 2008 (now U.S. Pat. No. 8,017,592), which is the National Stage of International Application Serial No.: PCT/US2007/066287 filed Apr. 10, 2007, which claims benefit to U.S. Provisional Patent Application Ser. No. 60/791,623 filed Apr. 13, 2006, the text of which is specifically incorporated by reference herein.

FIELD OF THE INVENTION

The present invention relates to the field of interfering RNA compositions for treatment of a histamine receptor H1 (HRH1)-related condition. Such conditions include allergic conjunctivitis, ocular inflammation, dermatitis, rhinitis, asthma, or allergy, for example.

BACKGROUND OF THE INVENTION

Allergic conjunctivitis, ocular inflammation, dermatitis, rhinitis, asthma, and allergy have historically been treated with a regimen of oral, intranasal or topical antihistamines, or oral or intranasal steroids, or, in the case of allergy, allergen injection treatment. Systemic treatment typically requires higher concentrations of the drug compound to be administered to afford an effective concentration to reach the necessary treatment site. Antihistamine compounds are known to have central nervous system activity; drowsiness and drying of mucus membranes are a common side-effect of antihistamine use.

Histamine binding to tissue histamine receptor H1 results in vascular leakage (edema), smooth muscle contraction (bronchoconstriction), or nerve fiber activation (pruritis, sneezing), for example. Many drugs including PATANOL® and EMADINE® exert a portion or all of their therapeutic effect by binding to this receptor.

Further agents and treatment methods would be desirable for targeting the histamine H1 receptor, thereby blocking the actions of endogenous histamine in the local environment while avoiding the side effects of systemic antihistamine treatment. Embodiments of the present invention address the need in the art for such agents and treatment methods.

SUMMARY OF THE INVENTION

Embodiments of the present invention overcome these and other drawbacks of the prior art by providing highly potent and efficacious treatment, prevention or intervention of an HRH1-related condition. In one aspect, methods of the invention include treating a subject having an HRH1-related condition or at risk of developing an HRH1-related condition by administering interfering RNAs that silence expression of HRH1 mRNA, thus interfering with the G-protein-coupled receptor signaling pathway and preventing a cascade of events related to histamine mediated inflammatory responses in an HRH1-related condition.

The present invention is directed to interfering RNAs that target HRH1 mRNA and thereby interfere with HRH1 mRNA expression. The interfering RNAs of the invention are useful for treating patients with an HRH1-related condition or at risk of developing an HRH1-related condition.

An embodiment of the invention is a method of attenuating expression of histamine receptor H1 mRNA of a subject, the method comprising administering to the subject a composition comprising an effective amount of interfering RNA having a length of 19 to 49 nucleotides and a pharmaceutically acceptable carrier. The expression of histamine receptor H1 mRNA is attenuated thereby.

Another embodiment of the invention is a method of treating an HRH1-related condition in a subject in need thereof. The method comprises administering to the subject a composition comprising an effective amount of interfering RNA having a length of 19 to 49 nucleotides, and a pharmaceutically acceptable carrier. The an HRH1-related condition is treated thereby. In one embodiment, the subject is a human and the human has an HRH1-related condition and, in another embodiment, the subject is a human and the human is at risk of developing an HRH1-related condition.

For the above cited embodiments, the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:2 and SEQ ID NO:13-SEQ ID NO:50.

In further embodiments of the above-cited methods, the composition further comprises a second interfering RNA having a length of 19 to 49 nucleotides and comprising a region of at least 13 contiguous nucleotides having at least 90% sequence complementarity to, or at least 90% sequence identity with, the penultimate 13 nucleotides of the 3' end of a second mRNA corresponding to any one of SEQ ID NO:2 and SEQ ID NO:13-SEQ ID NO:50.

In yet another embodiment of the invention, a method of attenuating expression of histamine receptor H1 mRNA of a subject comprises administering to the subject a composition comprising an effective amount of interfering RNA having a length of 19 to 49 nucleotides and a pharmaceutically acceptable carrier and the interfering RNA comprises a sense nucleotide strand, an antisense nucleotide strand, and a region of at least near-perfect contiguous complementarity of at least 19 nucleotides where the antisense strand hybridizes under physiological conditions to a portion of mRNA corresponding to SEQ ID NO:1, and has a region of at least near-perfect contiguous complementarity of at least 19 nucleotides with the hybridizing portion of mRNA corresponding to SEQ ID NO:1. The expression of histamine receptor H1 mRNA is attenuated thereby.

A method of treating an HRH1-related condition in a subject in need thereof is an embodiment of the invention, the method comprising administering to the subject a composition comprising an effective amount of interfering RNA having a length of 19 to 49 nucleotides, and a pharmaceutically acceptable carrier, the interfering RNA comprising a sense nucleotide strand, an antisense nucleotide strand, and a region of at least near-perfect contiguous complementarity of at least 19 nucleotides; wherein the antisense strand hybridizes under physiological conditions to a portion of mRNA corresponding to SEQ ID NO:1 and has a region of at least near-perfect contiguous complementarity of at least 19 nucleotides with the hybridizing portion of mRNA corresponding to SEQ ID NO:1. The an HRH1-related condition is treated thereby.

For the above-cited methods, the antisense strand of the interfering RNA is designed to target an mRNA corresponding to SEQ ID NO:1 comprising nucleotide 285, 324, 410, 581, 584, 660, 672, 801, 817, 1045, 1059, 1089, 1157, 1209, 1223, 1241, 1253, 1265, 1363, 1391, 1488, 1521, 1624, 1670, 1673, 1784, 1873, 1875, 1985, 2086, 2087, 2226, 2297, 2420, 2421, 2485, 2603, 2647, or 3431.

A second interfering RNA having a length of 19 to 49 nucleotides could also be administered to the subject; the second interfering RNA comprising a sense nucleotide strand, an antisense nucleotide strand, and a region of at least near-perfect complementarity of at least 19 nucleotides wherein the antisense strand of the second interfering RNA hybridizes under physiological conditions to a second portion of mRNA corresponding to SEQ ID NO:1, and the antisense strand has a region of at least near-perfect contiguous complementarity of at least 19 nucleotides with the second hybridizing portion of mRNA corresponding to SEQ ID NO:1.

A method of attenuating expression of histamine receptor H1 mRNA of a subject, comprising administering to the subject a composition comprising an effective amount of a single-stranded interfering RNA having a length of 19 to 49 nucleotides, and a pharmaceutically acceptable carrier, where the single-stranded interfering RNA hybridizes under physiological conditions to a portion of mRNA corresponding to SEQ ID NO:1 comprising the nucleotides identified above is a further embodiment of the invention.

A method of treating a HRH1-related condition in a subject in need thereof is an embodiment of the invention. The method comprises administering to the subject a composition comprising a double stranded siRNA molecule that down regulates expression of a HRH1 gene via RNA interference, wherein each strand of the siRNA molecule is independently about 19 to about 27 nucleotides in length; and one strand of the siRNA molecule comprises a nucleotide sequence having substantial complementarity to an mRNA corresponding to the HRH1 gene so that the siRNA molecule directs cleavage of the mRNA via RNA interference. In a further embodiment of this method, each strand of the siRNA molecule is independently about 19 nucleotides to about 25 nucleotides in length, or about 19 nucleotides to about 21 nucleotides in length.

A composition comprising a double stranded siRNA molecule that down regulates expression of a HRH1 gene via RNA interference is an embodiment of the invention. Each strand of the siRNA molecule is independently about 19 to about 27 nucleotides in length; and one strand of the siRNA molecule comprises a nucleotide sequence having substantial complementarity to an mRNA corresponding to the HRH1 gene so that the siRNA molecule directs cleavage of the mRNA via RNA interference. In a further embodiment of this composition, each strand of the siRNA molecule is independently about 19 nucleotides to about 25 nucleotides in length, or about 19 nucleotides to about 21 nucleotides in length.

The invention includes as a further embodiment a composition comprising an interfering RNA having a length of 19 to 49 nucleotides, and comprising a nucleotide sequence corresponding to any one of SEQ ID NO:2 and SEQ ID NO:13-SEQ ID NO:50, or a complement thereof; and a pharmaceutically acceptable carrier.

Use of any of the embodiments as described herein in the preparation of a medicament for attenuating expression of HRH1 mRNA as set forth herein is also an embodiment of the present invention.

DETAILED DESCRIPTION OF THE INVENTION

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

As used herein and unless otherwise indicated, the terms "a" and "an" are taken to mean "one", "at least one" or "one or more".

The term "an HRH1-related condition" as used herein, includes histamine mediated inflammatory responses involved in conditions such as allergic conjunctivitis, ocular inflammation, dermatitis, rhinitis, asthma, and allergy and includes those cellular changes resulting from the expression of HRH1-mRNA that lead directly or indirectly to the HRH1-related condition. The interfering RNA provided herein provides for such silencing while avoiding undesirable side effects due to nonspecific agents.

The term "allergic conjunctivitis," as used herein, refers to inflammation of the conjunctiva which is the delicate membrane that lines the eyelids and covers the exposed surface of the sclera. The term "allergic conjunctivitis" includes, for example, atopic keratoconjunctivitis, giant papillary conjunctivitis, hay fever conjunctivitis, perennial allergic conjunctivitis, and vernal keratoconjunctivitis.

The term "dermatitis," as used herein, refers to inflammation of the skin and includes, for example, allergic contact dermatitis, urticaria, asteatotic dermatitis (dry skin on the lower legs), atopic dermatitis, contact dermatitis including irritant contact dermatitis and urushiol-induced contact dermatitis, eczema, gravitational dermatitis, nummular dermatitis, otitis externa, perioral dermatitis, and seborrhoeic dermatitis.

The term "rhinitis," as used herein, refers to inflammation of the mucous membranes of the nose and includes, for example, allergic rhinitis, atopic rhinitis, irritant rhinitis, eosinophilic non-allergic rhinitis, rhinitis medicamentosa, and neutrophilic rhinosinusitis.

The term "asthma," as used herein, refers to inflammation of the air passages resulting in narrowing of the airways that transport air from the nose and mouth to the lungs and includes, for example, allergic asthma, atopic asthma, atopic bronchial IgE-mediated asthma, bronchial asthma, bronchiolytis, emphysematous asthma, essential asthma, exercise-induced asthma, extrinsic asthma caused by environmental factors, incipient asthma, intrinsic asthma caused by pathophysiologic disturbances, non-allergic asthma, non-atopic asthma, and wheezy infant syndrome.

The phrase "a region of at least 13 contiguous nucleotides having at least 90% sequence complementarity to, or at least 90% sequence identity with, the penultimate 13 nucleotides of the 3' end of an mRNA corresponding to any one of (a sequence identifier)" allows a one nucleotide substitution. Two nucleotide substitutions (i.e., $^{11}/_{13}$=85% identity/complementarity) are not included in such a phrase.

The term "percent identity" describes the percentage of contiguous nucleotides in a first nucleic acid molecule that is the same as in a set of contiguous nucleotides of the same length in a second nucleic acid molecule. The term "percent complementarity" describes the percentage of contiguous nucleotides in a first nucleic acid molecule that can base pair in the Watson-Crick sense with a set of contiguous nucleotides in a second nucleic acid molecule.

"Hybridization" refers to a process in which single-stranded nucleic acids with complementary or near-complementary base sequences interact to form hydrogen-bonded complexes called hybrids. Hybridization reactions are sensitive and selective. In vitro, the specificity of hybridization (i.e., stringency) is controlled by the concentrations of salt or formamide in prehybridization and hybridization solutions, for example, and by the hybridization temperature; such procedures are well known in the art. In particular, stringency is increased by reducing the concentration of salt, increasing the concentration of formamide, or raising the hybridization temperature.

For example, high stringency conditions could occur at about 50% formamide at 37° C. to 42° C. Reduced stringency conditions could occur at about 35% to 25% formamide at 30° C. to 35° C. Examples of stringency conditions for hybridization are provided in Sambrook, J., 1989, *Molecular Cloning: A Laboratory Manual*, Cold Spring Harbor Laboratory Press, Cold Spring Harbor, N.Y. Further examples of stringent hybridization conditions include 400 mM NaCl, 40 mM PIPES pH 6.4, 1 mM EDTA, 50° C. or 70° C. for 12-16 hours followed by washing, or hybridization at 70° C. in 1×SSC or 50° C. in 1×SSC, 50% formamide followed by washing at 70° C. in 0.3×SSC, or hybridization at 70° C. in 4×SSC or 50° C. in 4×SSC, 50% formamide followed by washing at 67° C. in 1×SSC. The temperature for hybridization is about 5-10° C. less than the melting temperature ($T_m$) of the hybrid where $T_m$ is determined for hybrids between 19 and 49 base pairs in length using the following calculation: $T_m°\ C.=81.5+16.6(\log_{10}[Na+])+0.41\ (\%\ G+C)-(600/N)$ where N is the number of bases in the hybrid, and [Na+] is the concentration of sodium ions in the hybridization buffer.

The term "allergy," as used herein, refers to an abnormal reaction of the immune system to a substance that is usually not harmful and includes, for example, skin allergies such as atopic dermatitis, hives, and angioedema; respiratory allergies such as allergic rhinitis, and reactions to dust or mold; food allergies such as reactions to proteins in cow's milk, egg whites, peanuts, wheat, soybeans, berries, shellfish, corn, beans, yellow food dye No. 5 and gum arabic; drug allergies such as reactions to penicillin, sulfas, barbiturates, anticonvulsants, insulin, local anesthetics and contrast agents; and insect bite allergies such as reactions to venom in stings of bees, wasps, hornets, yellow jackets and fire ants.

Attenuating expression of an mRNA: The phrase, "attenuating expression of an mRNA," as used herein, means administering or expressing an amount of interfering RNA (e.g., an siRNA) to reduce translation of the target mRNA into protein, either through mRNA cleavage or through direct inhibition of translation. The reduction in expression of the target mRNA or the corresponding protein is commonly referred to as "knock-down" and is reported relative to levels present following administration or expression of a non-targeting control RNA (e.g., a non-targeting control siRNA). Knock-down of expression of an amount including and between 50% and 100% is contemplated by embodiments herein. However, it is not necessary that such knock-down levels be achieved for purposes of the present invention. In one embodiment, a single interfering RNA targeting HRH1 mRNA is administered. In other embodiments, two or more interfering RNAs targeting HRH1 mRNA are administered.

Knock-down is commonly assessed by measuring the mRNA levels using quantitative polymerase chain reaction (qPCR) amplification or by measuring protein levels by western blot or enzyme-linked immunosorbent assay (ELISA). Analyzing the protein level provides an assessment of both mRNA cleavage as well as translation inhibition. Further techniques for measuring knock-down include RNA solution hybridization, nuclease protection, northern hybridization, gene expression monitoring with a microarray, antibody binding, radioimmunoassay, and fluorescence activated cell analysis.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaseIII-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini. One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the antisense strand) can favor incorporation of the antisense strand into RISC.

RISC-mediated cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA. Other RNA molecules and RNA-like molecules can also interact with RISC and silence gene expression. Examples of other RNA molecules that can interact with RISC include short hairpin RNAs (shRNAs), single-stranded siRNAs, microRNAs (miRNAs), and dicer-substrate 27-mer duplexes. The term "siRNA" as used herein refers to a double-stranded interfering RNA unless otherwise noted. Examples of RNA-like molecules that can interact with RISC include RNA molecules containing one or more chemically modified nucleotides, one or more deoxyribonucleotides, and/or one or more non-phosphodiester linkages. For purposes of the present discussion, all RNA or RNA-like molecules that can interact with RISC and participate in RISC-mediated changes in gene expression will be referred to as "interfering RNAs." SiRNAs, shRNAs, miRNAs, and dicer-substrate 27-mer duplexes are, therefore, subsets of "interfering RNAs."

Interfering RNA of embodiments of the invention appear to act in a catalytic manner for cleavage of target mRNA, i.e., interfering RNA is able to effect inhibition of target mRNA in substoichiometric amounts. As compared to antisense therapies, significantly less interfering RNA is required to provide a therapeutic effect under such cleavage conditions.

The present invention generally relates to the use of interfering RNA to inhibit the expression of histamine receptor H1 (HRH1) mRNA. The histamine H1 receptor (HRH1) is a member of the G protein-coupled receptor (GPCR) superfamily. Binding of histamine to HRH1 activates its associated heterotrimeric G protein, $G_{q/11}$, leading to activation of phospholipase C (PLC) and protein kinase C (PKC), synthesis of inositol 1,4,5-triphosphate (IP3) and 1,2-diacylglycerol, leading to a rise in intracellular $Ca^{2+}$, and other signaling events. Targeting the HRH1 mRNA thereby diminishes the local expression of HRH1, thus inhibiting the action of histamine in the local environment and interrupting the histamine mediated inflammatory responses. According to the present invention, interfering RNAs provided exogenously or expressed endogenously are particularly effective at silencing HRH1 mRNA.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

An mRNA sequence is readily deduced from the sequence of the corresponding DNA sequence. For example, SEQ ID NO:1 provides the sense strand sequence of DNA corresponding to the mRNA for HRH1. The mRNA sequence is identical to the DNA sense strand sequence with the "T" bases replaced with "U" bases. Therefore, the mRNA sequence of HRH1 is known from SEQ ID NO:1.

Histamine Receptor H1 (HRH1) mRNA: The GenBank database provides the DNA sequence for HRH1 as accession no. NM_000861, provided in the "Sequence Listing" as SEQ ID NO:1. SEQ ID NO:1 provides the sense strand sequence of DNA that corresponds to the mRNA encoding HRH1 (with the exception of "T" bases for "U" bases). The coding sequence for HRH1 is from nucleotides 179-1642.

Equivalents of the above cited HRH1 mRNA sequence are alternative splice forms, allelic forms, isozymes, or a cognate thereof. A cognate is a histamine receptor mRNA from another mammalian species that is homologous to SEQ ID NO:1 (i.e., an ortholog). HRH1 nucleic acid sequences related to SEQ ID NO:1 include those having GenBank accession numbers D14436, BC060802, Z34897, D28481, AB041380, X76786, AF026261, AY136743, and DQ047308.

Inhibition of HRH1 may also be determined in vitro using a human cell population that expresses HRH1. These cells would preferably be, but not limited to, primary human conjunctival epithelial cells as described by Cook et al. (Cook E B, et al. *Invest Ophthalmol Vis Sci*. 1998 February, 39(2):336-43) or the transformed human corneal epithelial cell line CEPI-17-CL4 (Offord E A, et al. *Invest Ophthalmol Vis Sci*. 1999 May, 40(6):1091-101). Evaluation of the activity of HRH1 interfering RNAs or controls can be performed by radioligand binding (Sharif N A, et al. *J Ocul Pharmacol Ther*. 1996 Winter, 12(4):401-7) where cells transfected with interfering RNA show diminished binding compared to cells transfected with a non-targeting control interfering RNA. Functional evaluation can be performed using calcium mobilization measured with a calcium sensitive dye in response to a histamine stimulus or using the production of [$^3$H]inositol phosphates ([$^3$H]IPs) as an index of receptor activation (Sharif N A, et al. *Invest Ophthalmol Vis Sci*. 1998 December, 39(13):2562-71). A diminished readout in interfering RNA treated cells compared to control indicates an inhibition of HRH1 function.

Inhibition of HRH1 may also be determined in vivo by preventing histamine induced vascular permeability changes in guinea pigs by prior treatment with an HRH1 targeted interfering RNA. A method for the in vivo study is provided by Yanni et al. (*J. Ocular Pharmacology* 10:665-675, 1994). Briefly, Dunkin Hartley outbred guinea pigs are injected intravenously via the marginal ear vein with 1.0 ml of Evans Blue dye. Forty-five minutes post dye injection, animals are challenged subconjunctivally with histamine. Local tissue responses can then be observed 30 minutes after histamine injection as an area of blue dye extravasated into the tissue of the conjunctiva. The interfering RNA is applied topically onto the eye 48-72 hours prior to histamine injection. A reduced change in vascular permeability in tissue treated with an interfering RNA demonstrates inhibition of HRH1 function.

Inhibition of HRH1 is also inferred in a human or mammal by observing an improvement in an HRH1-related condition symptom such as improvement in symptoms related to allergic conjunctivitis, ocular inflammation, dermatitis, rhinitis, asthma, or allergy. Improvement in any of edema, itching, inflammation, or tolerance to environmental challenges, for example, is indicative of inhibition of HRH1.

Interfering RNA: In one embodiment of the invention, interfering RNA (e.g., siRNA) has a sense strand and an antisense strand, and the sense and antisense strands comprise a region of at least near-perfect contiguous complementarity of at least 19 nucleotides. In a further embodiment of the invention, interfering RNA (e.g., siRNA) has a sense strand and an antisense strand, and the antisense strand comprises a region of at least near-perfect contiguous complementarity of at least 19 nucleotides to a target sequence of HRH1 mRNA, and the sense strand comprises a region of at least near-perfect contiguous identity of at least 19 nucleotides with a target sequence of HRH1 mRNA. In a further embodiment of the invention, the interfering RNA comprises a region of at least 13, 14, 15, 16, 17, or 18 contiguous nucleotides having percentages of sequence complementarity to or, having percentages of sequence identity with, the penultimate 13, 14, 15, 16, 17, or 18 nucleotides, respectively, of the 3' end of the corresponding target sequence within an mRNA.

The length of each strand of the interfering RNA comprises 19 to 49 nucleotides, and may comprise a length of 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 nucleotides.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression.

In embodiments of the present invention, interfering RNA target sequences (e.g., siRNA target sequences) within a target mRNA sequence are selected using available design tools. Interfering RNAs corresponding to an HRH1 target sequence are then tested by transfection of cells expressing the target mRNA followed by assessment of knockdown as described above.

Techniques for selecting target sequences for siRNAs are provided by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNAs.

An embodiment of a 19-nucleotide DNA target sequence for HRH1 mRNA is present at nucleotides 285 to 303 of SEQ ID NO:1:

```
5'-CTATCTGCTTGGTCACAGT-3'.    SEQ ID NO: 2
```

An siRNA of the invention for targeting a corresponding mRNA sequence of SEQ ID NO:2 and having 21-nucleotide strands and a 2-nucleotide 3' overhang is:

```
5'-CUAUCUGCUUGGUCACAGUNN-3'    SEQ ID NO: 3
3'-NNGAUAGACGAACCAGUGUCA-5'.   SEQ ID NO: 4
```

Each "N" residue can be any nucleotide (A, C, G, U, T) or modified nucleotide. The 3' end can have a number of "N" residues between and including 1, 2, 3, 4, 5, and 6. The "N" residues on either strand can be the same residue (e.g., UU, AA, CC, GG, or TT) or they can be different (e.g., AC, AG, AU, CA, CG, CU, GA, GC, GU, UA, UC, or UG). The 3' overhangs can be the same or they can be different. In one embodiment, both strands have a 3'UU overhang.

An siRNA of the invention for targeting a corresponding mRNA sequence of SEQ ID NO:2 and having 21-nucleotide strands and a 3'UU overhang on each strand is:

```
5'-CUAUCUGCUUGGUCACAGUUU-3'    SEQ ID NO: 5
3'-UUGAUAGACGAACCAGUGUCA-5'.   SEQ ID NO: 6
```

The interfering RNA may also have a 5' overhang of nucleotides or it may have blunt ends. An siRNA of the invention for targeting a corresponding mRNA sequence of SEQ ID NO:2 and having 19-nucleotide strands and blunt ends is:

```
5'-CUAUCUGCUUGGUCACAGU-3'     SEQ ID NO: 7
3'-GAUAGACGAACCAGUGUCA-5'.    SEQ ID NO: 8
```

The strands of a double-stranded interfering RNA (e.g., an siRNA) may be connected to form a hairpin or stem-loop structure (e.g., an shRNA). An shRNA of the invention targeting a corresponding mRNA sequence of SEQ ID NO:2 and having a 19 bp double-stranded stem region and a 3'UU overhang is:

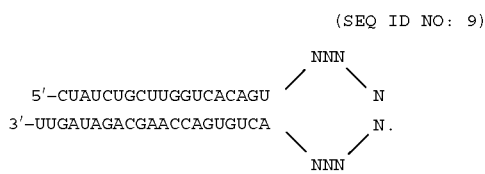

(SEQ ID NO: 9)

N is a nucleotide A, T, C, G, U, or a modified form known by one of ordinary skill in the art. The number of nucleotides N in the loop is a number between and including 3 to 23, or 5 to 15, or 7 to 13, or 4 to 9, or 9 to 11, or the number of nucleotides N is 9. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) *Science* 296: 550) and 5'-UUUGUGUAG-3' (Castanotto, D. et al. (2002) *RNA* 8:1454). It will be recognized by one of skill in the art that the resulting single chain oligonucleotide forms a stem-loop or hairpin structure comprising a double-stranded region capable of interacting with the RNAi machinery.

The siRNA target sequence identified above can be extended at the 3' end to facilitate the design of dicer-substrate 27-mer duplexes. Extension of the 19-nucleotide DNA target sequence (SEQ ID NO:2) identified in the HRH1 DNA sequence (SEQ ID NO:1) by 6 nucleotides yields a 25-nucleotide DNA target sequence present at nucleotides 285 to 309 of SEQ ID NO:1:

```
5'-CTATCTGCTTGGTCACAGTAGGGCT-3'.    SEQ ID NO: 10
```

A dicer-substrate 27-mer duplex of the invention for targeting a corresponding mRNA sequence of SEQ ID NO:10 is:

```
5'-CUAUCUGCUUGGUCACAGUAGGGCU-3'     SEQ ID NO: 11
3'-UUGAUAGACGAACCAGUGUCAUCCCGA-5'.  SEQ ID NO: 12
```

The two nucleotides at the 3' end of the sense strand (i.e., the CU nucleotides of SEQ ID NO:11) may be deoxynucleotides (i.e., TG) for enhanced processing. Design of dicer-substrate 27-mer duplexes from 19-21 nucleotide target sequences, such as provided herein, is further discussed by the Integrated DNA Technologies (IDT) website and by Kim, D.-H. et al., (February, 2005) *Nature Biotechnology* 23:2; 222-226.

When interfering RNAs are produced by chemical synthesis, phosphorylation at the 5' position of the nucleotide at the 5' end of one or both strands (when present) can enhance siRNA efficacy and specificity of the bound RISC complex but is not required since phosphorylation can occur intracellularly.

Further embodiments disclose various methods of attenuating expression of histamine receptor H1 mRNA of a subject, comprising:
administering to the subject a composition comprising an effective amount of interfering RNA having a length of 19 to 49 nucleotides and a pharmaceutically acceptable carrier, the interfering RNA comprising an RNA selected from the group consisting of:
a region of at least 13 contiguous nucleotides having at least 90% sequence complementarity to, or at least 90% sequence identity with, the penultimate 13 nucleotides of the 3' end of an mRNA corresponding to any one of SEQ ID NO:2 and SEQ ID NO:13-SEQ ID NO:50;
a region of at least 14 contiguous nucleotides having at least 85% sequence complementarity to, or at least 85% sequence identity with, the penultimate 14 nucleotides of the 3' end of an mRNA corresponding to any one of SEQ ID NO:2 and SEQ ID NO:13-SEQ ID NO:50; and,
a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to any one of SEQ ID NO:2 and SEQ ID NO:13-SEQ ID NO:50,
wherein the expression of histamine receptor H1 mRNA is attenuated thereby.

Also disclosed are methods of treating an HRH1-related condition in a subject in need thereof, comprising:
administering to the subject a composition comprising an effective amount of interfering RNA having a length of 19 to 49 nucleotides, and a pharmaceutically acceptable carrier, wherein the interfering RNA comprises a region of at least 13 contiguous nucleotides having at least 90% sequence complementarity to, or at least 90% sequence identity with, the penultimate 13 nucleotides of the 3' end of an mRNA corresponding to any one of SEQ ID NO:2 and SEQ ID NO:13-SEQ ID NO:50;

a region of at least 14 contiguous nucleotides having at least 85% sequence complementarity to, or at least 85% sequence identity with, the penultimate 14 nucleotides of the 3' end of an mRNA corresponding to any one of SEQ ID NO:2 and SEQ ID NO:13-SEQ ID NO:50; or, a region of at least 15, 16, 17, or 18 contiguous nucleotides having at least 80% sequence complementarity to, or at least 80% sequence identity with, the penultimate 15, 16, 17, or 18 nucleotides, respectively, of the 3' end of an mRNA corresponding to any one of SEQ ID NO:2 and SEQ ID NO:13-SEQ ID NO:50, wherein the an HRH1-related condition is treated thereby.

Other embodiments disclose various methods of attenuating expression of histamine receptor H1 mRNA of a subject, comprising:

administering to the subject a composition comprising an effective amount of interfering RNA having a length of 19 to 49 nucleotides and a pharmaceutically acceptable carrier, the interfering RNA comprising:

a sense nucleotide strand, an antisense nucleotide strand, and a region of at least near-perfect contiguous complementarity of at least 19 nucleotides;

wherein the antisense strand hybridizes under physiological conditions to a portion of mRNA corresponding to SEQ ID NO:1 and has a region of at least near-perfect contiguous complementarity of at least 19 nucleotides with the hybridizing portion of mRNA corresponding to SEQ ID NO:1, wherein the expression of histamine receptor H1 mRNA is attenuated thereby.

Various embodiments disclose methods of treating an HRH1-related condition in a subject in need thereof, comprising:

administering to the subject a composition comprising an effective amount of interfering RNA having a length of 19 to 49 nucleotides, and a pharmaceutically acceptable carrier, the interfering RNA comprising a sense nucleotide strand, an antisense nucleotide strand, and a region of at least near-perfect contiguous complementarity of at least 19 nucleotides;

wherein the antisense strand hybridizes under physiological conditions to a portion of mRNA corresponding to SEQ ID NO:1 and has a region of at least near-perfect contiguous complementarity of at least 19 nucleotides with the hybridizing portion of mRNA corresponding to SEQ ID NO:1, wherein the an HRH1-related condition is treated thereby.

Also disclosed are methods of attenuating expression of histamine receptor H1 mRNA of a subject, comprising:

administering to the subject a composition comprising an effective amount of a single-stranded interfering RNA having a length of 19 to 49 nucleotides, and a pharmaceutically acceptable carrier, wherein the single-stranded interfering RNA hybridizes under physiological conditions to a portion of mRNA corresponding to SEQ ID NO:1 comprising nucleotide 285, 324, 410, 581, 584, 660, 672, 801, 817, 1045, 1059, 1089, 1157, 1209, 1223, 1241, 1253, 1265, 1363, 1391, 1488, 1521, 1624, 1670, 1673, 1784, 1873, 1875, 1985, 2086, 2087, 2226, 2297, 2420, 2421, 2485, 2603, 2647, or 3431, and the interfering RNA has a region of at least near-perfect contiguous complementarity with the hybridizing portion of mRNA corresponding to SEQ ID NO:1, wherein the expression of histamine receptor H1 mRNA is thereby attenuated.

Also disclosed are methods of treating a HRH1-related condition in a subject in need thereof, comprising:

administering to the subject a composition comprising a double stranded siRNA molecule that down regulates expression of a HRH1 gene via RNA interference, wherein:

each strand of the siRNA molecule is independently about 19 to about 27 nucleotides in length; and one strand of the siRNA molecule comprises a nucleotide sequence having substantial complementarity to an mRNA corresponding to the HRH1 gene so that the siRNA molecule directs cleavage of the mRNA via RNA interference.

Further embodiments disclose a composition comprising a double stranded siRNA molecule that down regulates expression of a HRH1 gene via RNA interference, wherein:

each strand of the siRNA molecule is independently about 19 to about 27 nucleotides in length; and one strand of the siRNA molecule comprises a nucleotide sequence having substantial complementarity to an mRNA corresponding to the HRH1 gene so that the siRNA molecule directs cleavage of the mRNA via RNA interference.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

EXAMPLES

Table 1 lists examples of HRH1 DNA target sequences of SEQ ID NO:1 from which siRNAs of the present invention are designed in a manner as set forth above. HRH1 encodes histamine receptor H1, as noted above.

TABLE 1

HRH1 Target Sequences for siRNAs

| HRH1 Target Sequence | # of Starting Nucleotide with reference to SEQ ID NO: 1 | SEQ ID NO: |
|---|---|---|
| CTATCTGCTTGGTCACAGT | 285 | 2 |
| TGTATGCCGTACGGAGTGA | 324 | 13 |
| GCCGTCGTCATGCCTATGA | 410 | 14 |
| TACCTTAAGTATCGTACCA | 581 | 15 |

TABLE 1-continued

HRH1 Target Sequences for siRNAs

| HRH1 Target Sequence | # of Starting Nucleotide with reference to SEQ ID NO: 1 | SEQ ID NO: |
|---|---|---|
| CTTAAGTATCGTACCAAGA | 584 | 16 |
| CCATTCTAGGCTGGAATCA | 660 | 17 |
| GGAATCACTTCATGCAGCA | 672 | 18 |
| GGTTCTATGCCAAGATCTA | 801 | 19 |
| CTACAAGGCCGTACGACAA | 817 | 20 |
| CAGCCAAGAGGATGATAGA | 1045 | 21 |
| ATAGAGAAGTAGACAAACT | 1059 | 22 |
| CACTTGATATTGTGCACAT | 1089 | 23 |
| AGCCATGGCCAGCTCAAGA | 1157 | 24 |
| GCGAGATATCAGAGGATCA | 1209 | 25 |
| GATCAGATGTTAGGTGATA | 1223 | 26 |
| AGCCAATCCTTCTCTCGAA | 1241 | 27 |
| TCTCGAACGGACTCAGATA | 1253 | 28 |
| TCAGATACCACCACAGAGA | 1265 | 29 |
| CTCGCATTCAAGACAGTAT | 1363 | 30 |
| TTGCACATGAACCGCGAAA | 1391 | 31 |
| TCATTGCCTTCTGCAAGAA | 1488 | 32 |
| ATTTGCACATGTTCACCAT | 1521 | 33 |
| TCTGCATATTCGCTCCTAA | 1624 | 34 |
| TGATCCTTATGATGTCCAA | 1670 | 35 |
| TCCTTATGATGTCCAACAA | 1673 | 36 |
| AGTTCTTAGGCACCATAGA | 1784 | 37 |
| TCAGACCTGTTTCTTGTAA | 1873 | 38 |
| AGACCTGTTTCTTGTAACT | 1875 | 39 |
| CAGACTCATTGTAATTCAA | 1985 | 40 |
| CCTGGAATGGAGCTGTATA | 2086 | 41 |
| CTGGAATGGAGCTGTATAA | 2087 | 42 |
| TTAACAGCTTTCTCCAGAA | 2226 | 43 |
| TGTTTAGAGTGGATAGAAA | 2297 | 44 |
| TTGAATGGTTGCACGTTAA | 2420 | 45 |
| TGAATGGTTGCACGTTAAA | 2421 | 46 |
| GTACTAGGTTTATCTCATT | 2485 | 47 |
| TAGCTAGTTATGTGAGAAA | 2603 | 48 |
| TCAGCTTATTGTAGCATAT | 2647 | 49 |
| GCATACTCTATGTGATTTA | 3431 | 50 |

As cited in the examples above, one of skill in the art is able to use the target sequence information provided in Table 1 to design interfering RNAs having a length shorter or longer than the sequences provided in Table 1 by referring to the sequence position in SEQ ID NO:1 and adding or deleting nucleotides complementary or near complementary to SEQ ID NO:1.

The target RNA cleavage reaction guided by siRNAs and other forms of interfering RNA is highly sequence specific. In general, siRNA containing a sense nucleotide strand identical in sequence to a portion of the target mRNA and an antisense nucleotide strand exactly complementary to a portion of the target mRNA are siRNA embodiments for inhibition of mRNAs cited herein. However, 100% sequence complementarity between the antisense siRNA strand and the target mRNA, or between the antisense siRNA strand and the sense siRNA strand, is not required to practice the present invention. Thus, for example, the invention allows for sequence variations that might be expected due to genetic mutation, strain polymorphism, or evolutionary divergence.

In one embodiment of the invention, the antisense strand of the siRNA has at least near-perfect contiguous complementarity of at least 19 nucleotides with the target mRNA. "Near-perfect," as used herein, means the antisense strand of the siRNA is "substantially complementary to," and the sense strand of the siRNA is "substantially identical" to at least a portion of the target mRNA. "Identity," as known by one of ordinary skill in the art, is the degree of sequence relatedness between nucleotide sequences as determined by matching the order and identity of nucleotides between the sequences. In one embodiment, the antisense strand of an siRNA having 80% and between 80% up to 100% complementarity, for example, 85%, 90% or 95% complementarity, to the target mRNA sequence are considered near-perfect complementarity and may be used in the present invention. "Perfect" contiguous complementarity is standard Watson-Crick base pairing of adjacent base pairs. "At least near-perfect" contiguous complementarity includes "perfect" complementarity as used herein. Computer methods for determining identity or complementarity are designed to identify the greatest degree of matching of nucleotide sequences, for example, BLASTN (Altschul, S. F., et al. (1990) *J. Mol. Biol.* 215:403-410).

The relationship between a target mRNA (sense strand) and one strand of an siRNA (the sense strand) is that of identity. The sense strand of an siRNA is also called a passenger strand, if present. The relationship between a target mRNA (sense strand) and the other strand of an siRNA (the antisense strand) is that of complementarity. The antisense strand of an siRNA is also called a guide strand.

The penultimate base in a nucleic acid sequence that is written in a 5' to 3' direction is the next to the last base, i.e., the base next to the 3' base. The penultimate 13 bases of a nucleic acid sequence written in a 5' to 3' direction are the last 13 bases of a sequence next to the 3' base and not including the 3' base. Similarly, the penultimate 14, 15, 16, 17, or 18 bases of a nucleic acid sequence written in a 5' to 3' direction are the last 14, 15, 16, 17, or 18 bases of a sequence, respectively, next to the 3' base and not including the 3' base.

In one embodiment of the invention, the region of contiguous nucleotides is a region of at least 14 contiguous nucleotides having at least 85% sequence complementarity to, or at least 85% sequence identity with, the penultimate 14 nucleotides of the 3' end of an mRNA corresponding to the sequence identified by each sequence identifier. Two nucleotide substitutions (i.e., $^{12}/_{14}$=86% identity/complementarity) are included in such a phrase.

In a further embodiment of the invention, the region of contiguous nucleotides is a region of at least 15, 16, 17, or 18 contiguous nucleotides having at least 80% sequence complementarity to, or at least 80% sequence identity with, the penultimate 14 nucleotides of the 3' end of an mRNA corresponding to the sequence of the sequence identifier. Three nucleotide substitutions are included in such a phrase.

The target sequence in the mRNAs corresponding to SEQ ID NO:1 may be in the 5' or 3' untranslated regions of the mRNA as well as in the coding region of the mRNA.

One or both of the strands of double-stranded interfering RNA may have a 3' overhang of from 1 to 6 nucleotides, which may be ribonucleotides or deoxyribonucleotides or a mixture thereof. The nucleotides of the overhang are not base-paired. In one embodiment of the invention, the interfering RNA comprises a 3' overhang of TT or UU. In another embodiment of the invention, the interfering RNA comprises at least one blunt end. The termini usually have a 5' phosphate group or a 3' hydroxyl group. In other embodiments, the antisense strand has a 5' phosphate group, and the sense strand has a 5' hydroxyl group. In still other embodiments, the termini are further modified by covalent addition of other molecules or functional groups.

The sense and antisense strands of the double-stranded siRNA may be in a duplex formation of two single strands as described above or may be a single molecule where the regions of complementarity are base-paired and are covalently linked by a hairpin loop so as to form a single strand. It is believed that the hairpin is cleaved intracellularly by a protein termed dicer to form an interfering RNA of two individual base-paired RNA molecules.

Interfering RNAs may differ from naturally-occurring RNA by the addition, deletion, substitution or modification of one or more nucleotides. Non-nucleotide material may be bound to the interfering RNA, either at the 5' end, the 3' end, or internally. Such modifications are commonly designed to increase the nuclease resistance of the interfering RNAs, to improve cellular uptake, to enhance cellular targeting, to assist in tracing the interfering RNA, to further improve stability, or to reduce the potential for activation of the interferon pathway. For example, interfering RNAs may comprise a purine nucleotide at the ends of overhangs. Conjugation of cholesterol to the 3' end of the sense strand of an siRNA molecule by means of a pyrrolidine linker, for example, also provides stability to an siRNA.

Further modifications include a 3' terminal biotin molecule, a peptide known to have cell-penetrating properties, a nanoparticle, a peptidomimetic, a fluorescent dye, or a dendrimer, for example.

Nucleotides may be modified on their base portion, on their sugar portion, or on the phosphate portion of the molecule and function in embodiments of the present invention. Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2'-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

There may be a region or regions of the antisense interfering RNA strand that is (are) not complementary to a portion of SEQ ID NO:1. Non-complementary regions may be at the 3', 5' or both ends of a complementary region or between two complementary regions.

Interfering RNAs may be generated exogenously by chemical synthesis, by in vitro transcription, or by cleavage of longer double-stranded RNA with dicer or another appropriate nuclease with similar activity. Chemically synthesized interfering RNAs, produced from protected ribonucleoside phosphoramidites using a conventional DNA/RNA synthesizer, may be obtained from commercial suppliers such as Ambion Inc. (Austin, Tex.), Invitrogen (Carlsbad, Calif.), or Dharmacon (Lafayette, Colo.). Interfering RNAs are purified by extraction with a solvent or resin, precipitation, electrophoresis, chromatography, or a combination thereof, for example. Alternatively, interfering RNA may be used with little if any purification to avoid losses due to sample processing.

Interfering RNAs can also be expressed endogenously from plasmid or viral expression vectors or from minimal expression cassettes, for example, PCR generated fragments comprising one or more promoters and an appropriate template or templates for the interfering RNA. Examples of commercially available plasmid-based expression vectors for shRNA include members of the pSilencer series (Ambion, Austin, Tex.) and pCpG-siRNA (InvivoGen, San Diego, Calif.). Viral vectors for expression of interfering RNA may be derived from a variety of viruses including adenovirus, adeno-associated virus, lentivirus (e.g., HIV, FIV, and EIAV), and herpes virus. Examples of commercially available viral vectors for shRNA expression include pSilencer adeno (Ambion, Austin, Tex.) and pLenti6/BLOCK-iT™-DEST (Invitrogen, Carlsbad, Calif.). Selection of viral vectors, methods for expressing the interfering RNA from the vector and methods of delivering the viral vector are within the ordinary skill of one in the art. Examples of kits for production of PCR-generated shRNA expression cassettes include Silencer Express (Ambion, Austin, Tex.) and siXpress (Mirus, Madison, Wis.). A first interfering RNA may be administered via in vivo expression from a first expression vector capable of expressing the first interfering RNA and a second interfering RNA may be administered via in vivo expression from a second expression vector capable of expressing the second interfering RNA, or both interfering RNAs may be administered via in vivo expression from a single expression vector capable of expressing both interfering RNAs.

Interfering RNAs may be expressed from a variety of eukaryotic promoters known to those of ordinary skill in the art, including pol III promoters, such as the U6 or H1 promoters, or pol II promoters, such as the cytomegalovirus promoter. Those of skill in the art will recognize that these promoters can also be adapted to allow inducible expression of the interfering RNA.

Hybridization under Physiological Conditions: In certain embodiments of the present invention, an antisense strand of an interfering RNA hybridizes with an mRNA in vivo as part of the RISC complex.

The above-described in vitro hybridization assay provides a method of predicting whether binding between a candidate siRNA and a target will have specificity. However, in the context of the RISC complex, specific cleavage of a target can also occur with an antisense strand that does not demonstrate high stringency for hybridization in vitro.

Single-stranded interfering RNA: As cited above, interfering RNAs ultimately function as single strands. Single-stranded (ss) interfering RNA has been found to effect mRNA silencing, albeit less efficiently than double-stranded RNA. Therefore, embodiments of the present invention also provide for administration of a ss interfering RNA that hybridizes under physiological conditions to a portion of SEQ ID NO:1 and has a region of at least near-perfect contiguous complementarity of at least 19 nucleotides with the hybridizing portion of SEQ ID NO:1. The ss interfering RNA has a length of 19 to 49 nucleotides as for the ds interfering RNA cited above. The ss interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

SS interfering RNAs are synthesized chemically or by in vitro transcription or expressed endogenously from vectors or expression cassettes as for ds interfering RNAs. 5' Phosphate groups may be added via a kinase, or a 5' phosphate may be the result of nuclease cleavage of an RNA. Delivery is as for ds interfering RNAs. In one embodiment, ss interfering RNAs having protected ends and nuclease resistant modifications are administered for silencing. SS interfering RNAs may be dried for storage or dissolved in an aqueous solution. The solution may contain buffers or salts to inhibit annealing or for stabilization.

Hairpin interfering RNA: A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Mode of administration: Interfering RNA may be delivered via aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal administration, for example.

Administration may be directly to the eye by ocular tissue administration such as periocular, conjunctival, subtenon, intracameral, intravitreal, intraocular, subretinal, subconjunctival, retrobulbar, intracanalicular, or suprachoroidal administration; by injection, by direct application to the eye using a catheter or other placement device such as a retinal pellet, intraocular insert, suppository or an implant comprising a porous, non-porous, or gelatinous material; by topical ocular drops or ointments; or by a slow release device in the cul-de-sac or implanted adjacent to the sclera (transscleral) or within the eye. Intracameral injection may be through the cornea into the anterior chamber to allow the agent to reach the trabecular meshwork. Intracanalicular injection may be into the venous collector channels draining Schlemm's canal or into Schlemm's canal. Further modes of administration include tablets, pills, and capsules.

Administration may be directly to the ear via, for example, topical otic drops or ointments, slow release devices in the ear or implanted adjacent to the ear. Local administration includes otic intramuscular, intratympanic cavity and intracochlear injection routes of administration. Furthermore, agents can be administered to the inner ear by placement of a gelfoam, or similar absorbent and adherent product, soaked with the interfering RNA against the window membrane of the middle/inner ear or adjacent structure.

Administration may be directly to the lungs, via, for example, an aerosolized preparation, and by inhalation via an inhaler or a nebulizer, for example Subject: A subject in need of treatment for an HRH1-related condition or at risk for developing an HRH1-related condition is a human or other mammal having an HRH1-related condition or at risk of developing an HRH1-related condition, such as allergic conjunctivitis, ocular inflammation, dermatitis, rhinitis, asthma, or allergy for example, associated with undesired or inappropriate expression or activity of HRH1 as cited herein.

Ocular structures associated with such disorders may include the eye, retina, choroid, lens, cornea, trabecular meshwork, iris, optic nerve, optic nerve head, sclera, aqueous chamber, vitreous chamber, ciliary body, or posterior segment, for example.

Otic structures associated with such disorders may include the inner ear, middle ear, outer ear, tympanic cavity or membrane, cochlea, or Eustachian tube, for example.

Pulmonary structures associated with such disorders may include the nose, mouth, pharynx, larynx, bronchial tubes, trachea, carina (the ridge separating the opening of the right and left main bronchi), and lungs, particularly the lower lungs, such as bronchioli and alveoli.

A subject may also be an otic cell, a lung cell, an ocular cell, cell culture, organ or an ex vivo organ or tissue.

Formulations and Dosage: Pharmaceutical formulations comprise interfering RNAs, or salts thereof, of the invention up to 99% by weight mixed with a physiologically acceptable carrier medium such as water, buffer, saline, glycine, hyaluronic acid, mannitol, and the like.

Interfering RNAs of the present invention are administered as solids, solutions, suspensions, or emulsions. The following are examples of possible formulations embodied by this invention.

|  | Amount in weight % |
|---|---|
| Interfering RNA | up to 99; 0.1-99; 0.1-50; 0.5-10.0 |
| Hydroxypropylmethylcellulose | 0.5 |
| Sodium chloride | 0.8 |
| Benzalkonium Chloride | 0.01 |
| EDTA | 0.01 |
| NaOH/HCl | Qs pH 7.4 |
| Purified water (RNase-free) | Qs 100 Ml |

|  | Amount in weight % |
|---|---|
| Interfering RNA | up to 99; 0.1-99; 0.1-50; 0.5-10.0 |
| Phosphate Buffered Saline | 1.0 |
| Benzalkonium Chloride | 0.01 |
| Polysorbate 80 | 0.5 |
| Purified water (RNase-free) | q.s. to 100% |

|  | Amount in weight % |
|---|---|
| Interfering RNA | up to 99; 0.1-99; 0.1-50; 0.5-10.0 |
| Monobasic sodium phosphate | 0.05 |
| Dibasic sodium phosphate (anhydrous) | 0.15 |
| Sodium chloride | 0.75 |
| Disodium EDTA | 0.05 |

-continued

| | Amount in weight % |
|---|---|
| Cremophor EL | 0.1 |
| Benzalkonium chloride | 0.01 |
| HCl and/or NaOH | pH 7.3-7.4 |
| Purified water (RNase-free) | q.s. to 100% |

| | Amount in weight % |
|---|---|
| Interfering RNA | up to 99; 0.1-99; 0.1-50; 0.5-10.0 |
| Phosphate Buffered Saline | 1.0 |
| Hydroxypropyl-β-cyclodextrin | 4.0 |
| Purified water (RNase-free) | q.s. to 100% |

Generally, an effective amount of the interfering RNAs of embodiments of the invention results in an extracellular concentration at the surface of the target cell of from 100 pM to 100 nM, or from 1 nM to 50 nM, or from 5 nM to about 10 nM, or about 25 nM. The dose required to achieve this local concentration will vary depending on a number of factors including the delivery method, the site of delivery, the number of cell layers between the delivery site and the target cell or tissue, whether delivery is local or systemic, etc. The concentration at the delivery site may be considerably higher than it is at the surface of the target cell or tissue. Topical compositions are delivered to the surface of the target organ one to four times per day, or on an extended delivery schedule such as daily, weekly, bi-weekly, monthly, or longer, according to the routine discretion of a skilled clinician. The pH of the formulation is about pH 4-9, or pH 4.5 to pH 7.4.

Therapeutic treatment of patients with siRNAs directed against HRH1 mRNA is expected to be beneficial over small molecule treatments by increasing the duration of action, thereby allowing less frequent dosing and greater patient compliance.

An effective amount of a formulation may depend on factors such as the age, race, and sex of the subject, the severity of the HRH1-related condition, the rate of target gene transcript/protein turnover, the interfering RNA potency, and the interfering RNA stability, for example. In one embodiment, the interfering RNA is delivered topically to a target organ and reaches histamine receptor containing tissue at a therapeutic dose thereby ameliorating an HRH1-related process.

Acceptable carriers: An acceptable carrier refers to those carriers that cause at most, little to no ocular irritation, provide suitable preservation if needed, and deliver one or more interfering RNAs of the present invention in a homogenous dosage. Acceptable carriers for administration of interfering RNA of embodiments of the present invention include the cationic lipid-based transfection reagents TransIT®-TKO (Minis Corporation, Madison, Wis.), LIPOFECTIN®, Lipofectamine, OLIGOFECTAMINE™ (Invitrogen, Carlsbad, Calif.), or DHARMAFECT™ (Dharmacon, Lafayette, Colo.); polycations such as polyethyleneimine; cationic peptides such as Tat, polyarginine, or Penetratin (Antp peptide); or liposomes. Liposomes are formed from standard vesicle-forming lipids and a sterol, such as cholesterol, and may include a targeting molecule such as a monoclonal antibody having binding affinity for endothelial cell surface antigens, for example. Further, the liposomes may be PEGylated liposomes.

The interfering RNAs may be delivered in solution, in suspension, or in bioerodible or non-bioerodible delivery devices. The interfering RNAs can be delivered alone or as components of defined, covalent conjugates. The interfering RNAs can also be complexed with cationic lipids, cationic peptides, or cationic polymers; complexed with proteins, fusion proteins, or protein domains with nucleic acid binding properties (e.g., protamine); or encapsulated in nanoparticles. Tissue- or cell-specific delivery can be accomplished by the inclusion of an appropriate targeting moiety such as an antibody or antibody fragment.

For ophthalmic, otic, or pulmonary delivery, an interfering RNA may be combined with ophthalmologically, optically, or pulmonary acceptable preservatives, co-solvents, surfactants, viscosity enhancers, penetration enhancers, buffers, sodium chloride, or water to form an aqueous, sterile suspension or solution. Solution formulations may be prepared by dissolving the interfering RNA in a physiologically acceptable isotonic aqueous buffer. Further, the solutions may include an acceptable surfactant to assist in dissolving the inhibitor. Viscosity building agents, such as hydroxymethyl cellulose, hydroxyethyl cellulose, methylcellulose, polyvinylpyrrolidone, or the like may be added to the compositions of the present invention to improve the retention of the compound.

In order to prepare a sterile ointment formulation, the interfering RNA is combined with a preservative in an appropriate vehicle, such as mineral oil, liquid lanolin, or white petrolatum. Sterile gel formulations may be prepared by suspending the interfering RNA in a hydrophilic base prepared from the combination of, for example, CARBOPOL®-940 (BF Goodrich, Charlotte, N.C.), or the like, according to methods known in the art. VISCOAT® (Alcon Laboratories, Inc., Fort Worth, Tex.) may be used for intraocular injection, for example. Other compositions of the present invention may contain penetration enhancing agents such as cremephor and TWEEN® 80 (polyoxyethylene sorbitan monolaureate, Sigma Aldrich, St. Louis, Mo.), in the event the interfering RNA is less penetrating in the organ or tissue of interest.

Kits: Embodiments of the present invention provide a kit that includes reagents for attenuating the expression of an mRNA as cited herein in a cell. The kit contains an siRNA or an shRNA expression vector. For siRNAs and non-viral shRNA expression vectors the kit also may contain a transfection reagent or other suitable delivery vehicle. For viral shRNA expression vectors, the kit may contain the viral vector and/or the necessary components for viral vector production (e.g., a packaging cell line as well as a vector comprising the viral vector template and additional helper vectors for packaging). The kit may also contain positive and negative control siRNAs or shRNA expression vectors (e.g., a non-targeting control siRNA or an siRNA that targets an unrelated mRNA). The kit also may contain reagents for assessing knockdown of the intended target gene (e.g., primers and probes for quantitative PCR to detect the target mRNA and/or antibodies against the corresponding protein for western blots). Alternatively, the kit may comprise an siRNA sequence or an shRNA sequence and the instructions and materials necessary to generate the siRNA by in vitro transcription or to construct an shRNA expression vector.

A pharmaceutical combination in kit form is further provided that includes, in packaged combination, a carrier means adapted to receive a container means in close confinement therewith and a first container means including an interfering RNA composition and an acceptable carrier. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit.

The ability of HRH1 interfering RNA to knock-down the levels of endogenous HRH1 expression in, for example, human corneal epithelial cells is evaluated in vitro as follows. Transformed human corneal epithelial cells, for example, the CEPI-17 cell line (Offord et al. (1999) *Invest Ophthalmol Vis Sci.* 40:1091-1101), are plated 24 h prior to transfection in KGM keratinocyte medium (Cambrex, East Rutherford, N.J.). Transfection is performed using DharmaFECT™1 (Dharmacon, Lafayette, Colo.) according to the manufacturer's instructions at HRH1 interfering RNA concentrations ranging from 0.1 nM-100 nM. Non-targeting control interfering RNA and lamin A/C interfering RNA (Dharmacon) are used as controls. Target mRNA levels are assessed by qPCR 24 h post-transfection using, for example, TAQMAN® forward and reverse primers and a probe set that encompasses the target site (Applied Biosystems, Foster City, Calif.). Target protein levels may be assessed approximately 72 h post-transfection (actual time dependent on protein turnover rate) by western blot, for example. Standard techniques for RNA and/or protein isolation from cultured cells are well-known to those skilled in the art. To reduce the chance of non-specific, off-target effects, the lowest possible concentration of HRH1 interfering RNA should be used that will produce the desired level of knock-down in target gene expression.

The references cited herein, to the extent that they provide exemplary procedural or other details supplementary to those set forth herein, are specifically incorporated by reference.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

What is claimed is:

1. A method of attenuating expression of histamine receptor H1 mRNA of a subject, comprising:
administering to the subject a composition comprising an effective amount of interfering RNA having a length of 19 to 49 nucleotides and a pharmaceutically acceptable carrier, the interfering RNA comprising
a region of at least 17 contiguous nucleotides having at least 85% sequence complementarity to, or at least 85% sequence identity with, the penultimate 17 nucleotides of the 3' end of an mRNA corresponding to SEQ ID NO: 30,
wherein the expression of histamine receptor H1 mRNA is attenuated thereby.

2. The method of claim 1, wherein the composition further comprises a second interfering RNA having a length of 19 to 49 nucleotides and comprising a region of at least 17 contiguous nucleotides having at least 90% sequence complementarity to, or at least 90% sequence identity with, the penultimate 17 nucleotides of the 3' end of a second mRNA corresponding to any one of SEQ ID NO:2 and SEQ ID NO:13-SEQ ID NO:50.

3. The method of claim 1, wherein the interfering RNA is an shRNA.

4. The method of claim 1, wherein the composition is administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

5. The method of claim 1, wherein the interfering RNA is administered via in vivo expression from an expression vector capable of expressing the interfering RNA.

6. The method hod of claim 1, wherein the interfering RNA is an siRNA.

7. A method of treating an HRH1-related condition in a subject in need thereof, comprising:
administering to the subject a composition comprising an effective amount of interfering RNA having a length of 19 to 49 nucleotides, and a pharmaceutically acceptable carrier, wherein
a region of at least 17 contiguous nucleotides having at least 85% sequence complementarity to, or at least 85% sequence identity with, the penultimate 17 nucleotides of the 3' end of an mRNA corresponding to SEQ ID NO: 30,
wherein the an HRH1-related condition is treated thereby.

8. The method of claim 7, wherein the composition further comprises a second interfering RNA having a length of 19 to 49 nucleotides and comprising a region of at least 17 contiguous nucleotides having at least 90% sequence complementarity to, or at least 90% sequence identity with, the penultimate 17 nucleotides of the 3' end of a second mRNA corresponding to any one of SEQ ID NO:2 and SEQ ID NO:13-SEQ ID NO:50.

9. The method of claim 7, wherein the interfering RNA is an shRNA.

10. The method of claim 7, wherein the composition is administered via an aerosol, buccal, dermal, intradermal, inhaling, intramuscular, intranasal, intraocular, intrapulmonary, intravenous, intraperitoneal, nasal, ocular, oral, otic, parenteral, patch, subcutaneous, sublingual, topical, or transdermal route.

11. The method of claim 7, wherein the interfering RNA is administered, via in vivo expression from an expression vector capable of expressing the interfering RNA.

12. The method of claim 7, wherein the interfering RNA is an siRNA.

13. The method of claim 7, wherein the subject is a human and the human has an HRH1-related condition or is at risk of developing an HRH1-related condition.

* * * * *